US011519897B2

(12) United States Patent
Peña Díez et al.

(10) Patent No.: US 11,519,897 B2
(45) Date of Patent: Dec. 6, 2022

(54) COMPUTER IMPLEMENTED METHOD FOR CHARACTERIZING A TARGET FLUID OF A HYDROCARBON RESERVOIR UNDER UNCERTAINTY

(71) Applicant: Repsol, S.A., Madrid (ES)

(72) Inventors: José Luís Peña Díez, Madrid (ES); Daniel Merino García, Madrid (ES); Verónica Benito Iglesias, Madrid (ES); Paula Sanz Sanz, Madrid (ES)

(73) Assignee: Repsol, S.A., Madrid (ES)

(*) Notice: Subject to any disclaimer, the term of this patent is extended or adjusted under 35 U.S.C. 154(b) by 38 days.

(21) Appl. No.: 16/497,632

(22) PCT Filed: Mar. 27, 2018

(86) PCT No.: PCT/EP2018/057714
§ 371 (c)(1),
(2) Date: Sep. 25, 2019

(87) PCT Pub. No.: WO2018/178045
PCT Pub. Date: Oct. 4, 2018

(65) Prior Publication Data
US 2020/0103389 A1 Apr. 2, 2020

(30) Foreign Application Priority Data
Mar. 29, 2017 (EP) .................................. 17382158

(51) Int. Cl.
G01N 33/28 (2006.01)
E21B 47/06 (2012.01)
(Continued)

(52) U.S. Cl.
CPC ......... *G01N 33/2823* (2013.01); *E21B 47/06* (2013.01); *E21B 47/07* (2020.05);
(Continued)

(58) Field of Classification Search
CPC ...... E21B 49/082; E21B 47/06; E21B 49/081; E21B 49/0875; G01N 33/2823; G06F 17/15
See application file for complete search history.

(56) References Cited

U.S. PATENT DOCUMENTS

| 2006/0155474 | A1 | 7/2006 | Venkataramanan et al. |
| 2014/0278113 | A1* | 9/2014 | Chok ............... E21B 49/088 702/13 |
| 2017/0075028 | A1* | 3/2017 | Bang ............... G01N 33/2823 |

FOREIGN PATENT DOCUMENTS

| WO | WO-2011007268 A1 * | 1/2011 | ........... E21B 49/082 |
| WO | WO2011007268 A1 | 1/2011 | |

OTHER PUBLICATIONS

Merino-Garcia "An innovative approach for formation fluid typing with API and GOR assessments in real time from mud gas data" (Year: 2014).*

(Continued)

*Primary Examiner* — Catherine T. Rastovski
*Assistant Examiner* — Kaleria Knox
(74) *Attorney, Agent, or Firm* — Reising Ethington P.C.

(57) ABSTRACT

The present invention is related to computer implemented method for characterizing a target fluid of a hydrocarbon reservoir under uncertainty providing a set of fluid properties from a limited amount of information.

16 Claims, 7 Drawing Sheets

(51) Int. Cl.
*E21B 49/08* (2006.01)
*G06F 17/15* (2006.01)
*E21B 47/07* (2012.01)

(52) U.S. Cl.
CPC ............ *E21B 49/081* (2013.01); *G06F 17/15* (2013.01); *E21B 49/0875* (2020.05)

(56) References Cited

OTHER PUBLICATIONS

D Merino-Garcia et al., "An Innovative Approach for Formation Fluid Typing with API and GOR Assessments in Real Time from Mud Gas Data", 76th Eage Conference and Exhibition, Jun. 19, 2014, pp. 16-19, XP055408226 (5 pages).
International Search Report for International Application No. PCT/EP2018/057714 dated Jun. 22, 2018 (4 pages).

\* cited by examiner

| PARAMETER | VALUE |
|---|---:|
| Fluid ID | 34 |
| Reservoir ID | 63 |
| API Gravity | 35 |
| GOR | 2 |
| Kerogen Type | 2 |
| Source Rock | 3 |
| Source Rock Perid | 380 |
| Maturation Level | ? |
| Fluid Mixing Evidence | YES=1 |
| Washing Evidence | NO=2 |
| … | … |

FIG. 2

| TSR Evidence | Value |
|---|---|
| YES | 1 |
| NO | 0 |
| | |
| Washing Evidence | Value |
| YES | 1 |
| NO | 0 |
| | |
| Fluid Mixing Evidence | Value |
| YES | 1 |
| NO | 0 |

FIG.4

| Kerogen Type | Value |
|---|---|
| I | 1 |
| II | 2 |
| III | 3 |
| | |
| Source Rock Type | Value |
| Carbonate | 1 |
| Marl | 2 |
| Shale | 3 |

FIG.5

| Fluid ID | Value |
|---|---|
| Heavy Oil | 1 |
| Black Oil | 2 |
| Volatile Oil | 3 |
| Near Critical | 4 |
| Gas Condensate | 5 |
| Wet Gas | 6 |
| Dry Gas | 7 |

FIG.6A

| Source Rock Period | Average Age |
|---|---|
| Pre-Cambrian | 540 |
| Cambrian | 520 |
| Ordovician | 460 |
| Silurian | 422 |
| Devonian | 380 |
| Carboniferous | 325 |
| Permic | 272 |
| Triassic | 230 |
| Jurassic | 167 |
| Cretacic | 96 |
| Paleogene | 37 |
| Neogene | 11 |

FIG.6B

| Maturation Level (Vreq) | Value |
|---|---|
| Immature | 1 |
| Early | 2 |
| Peak | 3 |
| Late | 4 |
| Wet Gas | 5 |
| Dry Gas | 6 |

FIG.6C

| Biodegradation (Moldowan Index) | Value |
|---|---|
| 1 | 1 |
| 2 | 2 |
| 3 | 3 |
| 4 | 4 |
| 5 | 5 |
| 6 | 6 |
| 7 | 7 |
| 8 | 8 |
| 9 | 9 |
| 10 | 10 |

FIG.6D

COMPUTER IMPLEMENTED METHOD FOR CHARACTERIZING A TARGET FLUID OF A HYDROCARBON RESERVOIR UNDER UNCERTAINTY

RELATED APPLICATION

This application is the National Stage of International Patent Application No. PCT/EP2018/057714, filed on Mar. 27, 2018.

FIELD OF THE INVENTION

The present invention is related to computer implemented method for characterizing a target fluid of a hydrocarbon reservoir under uncertainty providing a set of fluid properties from a limited amount of information.

PRIOR ART

One of the technical fields with a more intensive development is the characterization process of hydrocarbon reservoirs defining physical and chemical properties, among others, and other parameters of the rock and fluids of said reservoirs that are relevant to assess the amount of recoverable hydrocarbon resources from the reservoir and for subsequently determining facilities to be deployed in the field.

Facilities must be designed according to the properties of the fluid to be recovered as the flow along the conduits from the reservoir to the surface evolves with pressure and temperature variations that may cause phase changes appearing solid parts that may difficult or even obstruct the conduit preventing the normal production process.

In most of the cases, the hydrocarbon resources and, specifically the fluids located within the reservoir, cannot be easily retrieved preventing the subsequent analysis of the samples that provides property characterization of the fluid stored in the reservoir.

Even when samples are obtained from well tests or after drilling operations, samples arriving to the laboratory are under very different conditions to the ones that are in the reservoir. In some other cases, samples are contaminated, increasing the uncertainty of the properties measured in the laboratory.

In most of the cases, in order to predict fluid properties when no sample is available, the skilled person carry out a previous work of basin modeling by using commercial programs applied to predict the evolution of the basin along long periods of time.

These programs simulate the hydrocarbon generation at high pressure and temperature in the source rock and the migration of the fluid from the source rock to the formation rock or reservoir.

These programs also take into account processes occurring during the migration that may modify the final fluid properties.

As a result of this work, in many cases, data of API gravity (American Petroleum Institute gravity, being a well-known density variable) and GOR (gas-oil ratio when the reservoir fluid is taken to ambient conditions) of the reservoir fluid is obtained.

According to the prior art, the skilled person associates the API and GOR properties with other fluids known in literature estimating the rest of properties.

It is not known by the applicant a process that automatically characterize the fluid properties allowing to provide property values not subjected to the subjective interpretation of the skilled person.

DESCRIPTION OF THE INVENTION

The present invention solves the posed problem providing a method that may be implemented in a computer providing a set of characterizing properties defined by their density functions.

Therefore, the present invention is a computer implemented method for characterizing a target fluid of a hydrocarbon reservoir under uncertainty by means of m predetermined fluid properties. Among said m fluid properties the method at least comprises a first fluid property ($p_1$) directed to one of the phases of the target fluid, either liquid or gas, and a second fluid property ($p_2$) directed to the gas/liquid ratio of the target fluid.

In a preferred embodiment, the first fluid property ($p_1$) is the API gravity of one of the phases and the GOR of the target fluid, being the target fluid the fluid to be characterized by using the limited amount of data obtained from the reservoir.

The method comprises the following steps:
a) assigning a probability density function ($f_1$) for the first fluid property ($p_1$) and a probability density function ($f_2$) for the second fluid property ($p_2$);
b) providing m−2 correlations $c_3, \ldots, c_m$ dependent at least on $p_1$ and/or $p_2$ properties such that $p_i = c_i(p_1, p_2)$; $i = 3 \ldots, m$;
c) for each property $p_i$, $i = 3, \ldots, m$
    generating, automatically by a computer system, r sample values $c_i(\tilde{p}_1, \tilde{p}_2)$ wherein $\tilde{p}_1$ is a random sample according to its probability density function $f_1$ and $\tilde{p}_2$ is a random sample according to its probability density function $f_2$;
    generating, automatically by a computer system, a probability density function $f_i$ for property $p_i$ from the r sample values $c_i(\tilde{p}_1, \tilde{p}_2)$;
d) making available the characterizing properties $p_i$, $i = 1, \ldots, m$ of the fluid as the probability density functions ($f_1, f_2, \ldots, f_m$).

For the first fluid property ($p_1$) and for the second fluid property ($p_2$) probability density functions ($f_1$ and $f_2$ respectively) are imposed. A uniform function or a Gaussian function is a probability density function appropriate in most of the cases. In some embodiments, the probability density function is defined only by means of a discrete set of values such as three percentiles, a $p_{low}$-percentile, a $p_{mean}$-percentile and a $p_{high}$-percentile. In a preferred embodiment $p_{low}$ is $p_{10}$, $p_{mean}$ is $p_{50}$ and $p_{high}$ is $p_{90}$ respectively. In a preferred embodiment the random sampling step is a Montecarlo method.

The method requires to provide a correlation $c_i$ per each property $p_i$, $i = 3, \ldots, m$ at least depending on $p_1$ and/or $p_2$. For each property $p_i$, the fluid properties being involved in the dependency of $c_i$, that is, the first fluid property $p_1$, the second fluid property $p_2$ or both, are randomly sampled ($\tilde{p}_1$, $\tilde{p}_2$) according to its probability density function. A new probability density function $f_i$ is generated from the sampled values $c_i(\tilde{p}_1, \tilde{p}_2)$.

In another embodiment, $c_i$ correlations depend on additional properties $p_i$ $i > 3$. In such cases the fluid properties $p_i$, $i = 3, \ldots, m$ are sorted such that dependency of correlations is $c_3 = c_3(p_1, p_2)$, $c_4 = c_4(p_1, p_2, p_3), \ldots, c_i = c_i(p_1, p_2, \ldots, p_{i-1})$ wherein not necessarily all properties $p_3, \ldots, p_{i-1}$ appear explicitly as dependent parameters. In these cases the probability density functions $f_i$ corresponding to property $p_i$ i>3 when determining $p_j$,j>i are available as they have been determined in previous steps.

In another embodiment, $c_i$ correlations are automatically corrected by the computer system carrying out the method before using them for determining a certain property $p_i$ by using the knowledge provided by an analogous data base. After this correction the $c_i$ correlations represent correctly the properties stored in the analogous data base and then the target fluid.

Analogous data bases comprise fluid properties obtained from reservoirs that have already been exploited. Among the available data records of analogous data bases comprise binary variables, multiple binary variables, quantitative variables or any combination of them.

Examples of binary variables are indicators of TSR Evidence, Washing Evidence or Fluid Mixing Evidence.

Examples of multiple binary variables are variables representing Kerogen Type (I, II or III) or The Source Rock type (Carbonate, Marl, Shale, etc.).

Examples of quantitative variables are "Fluid ID" (taking integer values), average age of source rock period, the maturation level or the biodegradation for instance using the Moldowan Index (integer value).

According to this embodiment, at least one record of the analog data base comprises the first fluid property ($p_1$), the second fluid property ($p_2$) or both; being these properties the common property allowing to extract relevant information from analog fluids. These common properties allowing the selection will be identified as key properties.

A similarity module is in charge of the comparison of fluid properties of the target fluid and fluid properties of records of the analog data base, the module providing a similarity value as a result of said comparison. This module may be implemented in a computer system as a function returning the similarity value or even a pointer to a more complex record providing additional information obtained in the comparison process.

Two key values of properties are deemed to be similar if the absolute value of the difference is lower than a predetermined threshold parameter (sim). Those records having similar key values when compared to a target fluid, in view of the threshold parameter, are being deemed to be selected.

The selection of analogous records may comprise additional constraints taking into account properties related to the physical, chemical and geological properties of the reservoir, and also to properties having an impact on the transportation of the hydrocarbon fluid from the reservoir to the surface, mainly those properties taken into account when ensuring the flow during the exploitation of the reservoir.

Once the selected records are identified, the correlation $c_i$ is modified by shifting it by a first C constant value and being scaled by a second $\Delta c_i$ constant value. The selected records are being sampled and constants C, $\Delta c_i$ are determined by imposing that the sum of errors between the value provided by the new correlation $c'_i = c_i * C + \Delta c_i$ and the property value provided by the samples of the selected records of the analog data base is minimum.

Then, in step c) of the method according to the invention, the modified correlation. $c'_i$ is used when the r sample values $c_i(\tilde{p}_1, \tilde{p}_2)$ are computed.

As it was identified above, analogue data bases may involve at least three kinds of variables, binary variables, multiple binary variables, quantitative variables when comparing the target fluid and the analogue fluids by means of the similarity module in order to determine the selected records. In this comparison process each kind of variable has a contribution value to the similarity value being part of the total similarity value. This contribution value is determined according to specific rules weighing the relevance of the property.

If the target fluid and at least one record of the analogous data base comprise at least one binary property, then according to an embodiment, each type of the binary properties is set to 0 or 1 and comprises a weighing value.

In this particular case the binary property is set to 0 or 1, but other two values may be used weighing the resulting value by a scalar value accordingly responsive to the two arbitrarily selected values. That is, the use of any other two values is deemed to be equivalent to the values used according to this embodiment.

In the particular case of binary variables the similarity module comprises a binary property contribution value, said contribution value being weighed with the weighing value, said weighing value determined according to the following rules for each binary property:

if the target fluid does not have the binary property and/or the record does not have the binary property, then the contribution value to the similarity value is set to 0 and the weighing value of the binary property is not taken into account;

if the target fluid and the record have the binary property but the target fluid value is different to the record value the contribution value to the similarity value is set to 0 so it does not account the weighing value of the property;

if the target fluid and the record have the binary property and the target fluid value is equal to the record value the weighing value is set to 1 so the full weighing value of the property is the contribution value to the similarity value.

If the target fluid and at least one record of the analogous data base comprise at least one multiple binary property, then according to an embodiment, each type of the multiple binary properties is set to 0 or 1 and comprises a weighing value.

In this particular case the multiple binary property is set to 0 or 1 but other two values may also be used weighing the resulting value by a scalar value accordingly responsive to the two arbitrarily selected values. That is, the use of any other two values for is deemed to be equivalent to the values used according to this embodiment.

In the particular case of binary variables each type of the multiple binary property comprises a weighing value and, the similarity module comprises a multiple binary property contribution value, said contribution value being weighed with the weighing value, said weighing value determined according to the following rules for each multiple binary property:

if the target fluid does not have the multiple binary property and/or the record does not have the multiple binary property, then the contribution value to the similarity value is set to 0 and the weighing value of the multiple binary property is not taken into account;

if the target fluid and the record have not in common any of the multiple integer combination of values, the contribution value to the similarity value is set to 0 and the weighing value of the property is not taken into account;

if the target fluid and the record have in common at least one of the multiple integer combination of values, the weighing value is set to 1 so the full weighing value of the property is the contribution value to the similarity value.

If the target fluid and at least one record of the analogous data base comprise at least one quantitative property, said quantitative property is represented by an integer or by a real number.

In the particular case of quantitative properties each type of the quantitative properties has a continuous value and comprises a weighing value and, the similarity module comprises a quantitative property contribution value, said contribution value being weighed with the weighing value, said weighing value determined according to the following rules for each quantitative property:
- if the target fluid does not have the continuous value property and/or the record does not have the continuous value property, then the contribution value to the similarity value is set to 0 and the weighing value of the quantitative property is not taken into account;
- if the target fluid and the record have the same quantitative property the contribution value to the similarity value is weighed by the weighing value:

$$\left(1 - \frac{|Vc_{ih} - Vc_{jh}|}{G_h}\right)$$

wherein $Vc_{ih}$ is the $h^{th}$ fluid quantitative property $Vc_i$ of the target fluid among the Vc quantitative properties of the target fluid, being Vc the number of quantitative variables of the target fluid;

$Vc_{jh}$ is the $h^{th}$ fluid quantitative property $Vc_j$ of the analog record among the Vc quantitative properties of the target fluid; and $G_h$ is the common range of the $h^{th}$ quantitative variables $Vc_i$ and $Vc_j$.

According to an embodiment, similarity value $s_{ij}$ between a target fluid and a record from the analog data base may involve binary properties, multiple binary properties and quantitative properties. In this particular case the similarity value $s_{ij}$ may be expressed in a single expression involving the three kinds of properties and wherein if any kind of the properties does not exist the contribution terms are zero. In such case the single expression may be expressed as:

$$s_{ij} = \frac{\sum_{h=1}^{Vc}\left(\left(1 - \frac{|Vc_{ih} - Vc_{jh}|}{G_h}\right)Pc_h\right) + \sum_{k=1}^{Vb}(Vb_k * Pb_k) + \sum_{l=1}^{Vmb}(Vmb_l * Pmb_l)}{Pc_t + Pb_t + Pmb_t}$$

wherein, additionally to the former definitions:
$Pc_h$ is a weighing value of the $h^{th}$ quantitative variable;
Vb is the number of binary variables of the target fluid;
$Vb_k$ is a coincidence value, 1 if there is coincidence or 0 otherwise, for the $k^{th}$ binary variable of the target fluid;
$Pb_k$ is a weighing value for the $k^{th}$ binary variable
Vmb is the number of multiple binary variables of the target fluid;
$Vmb_l$ is a coincidence value, 1 if there is coincidence or 0 otherwise, for the $l^{th}$ multiple binary variable of the target fluid;
$Pmb_l$ is a weighing value of the $l^{th}$ multiple binary variable;
$Pc_t$ is the total weight of the quantitative variables;
$Pb_t$ is the total weight of the binary variables;
$Pmb_t$ is the total weight of the multiple binary variables.

DESCRIPTION OF THE DRAWINGS

These and other features and advantages of the invention will be more clearly seen from the following detailed description of a preferred embodiment provided only by way of illustrative and non-limiting example in reference to the attached drawings.

FIG. 2 This figure shows an example of table with a record storing the properties of a fluid, a target fluid or an analogous fluid. The property is disclosed by means of the name of the "parameter", column 1, and the property value shown in column 2.

FIG. 4 This figure shows three binary properties being defined as a Boolean value, (yes or no, true or false, for example) and, in column 2, the assigned value in this specific embodiment.

FIG. 5 This figure shows two multiple binary properties where column 2 shows the assigned value in this specific embodiment.

FIGS. 6A-6D These figures shows examples of quantitative values, Fluid ID, source Rock Period, Maturation Level or the Biodegradation (Moldowan Index). Column 2 shows the quantitative value for a set of the status of the continuous parameter.

DETAILED DESCRIPTION OF THE INVENTION

Figure 1:
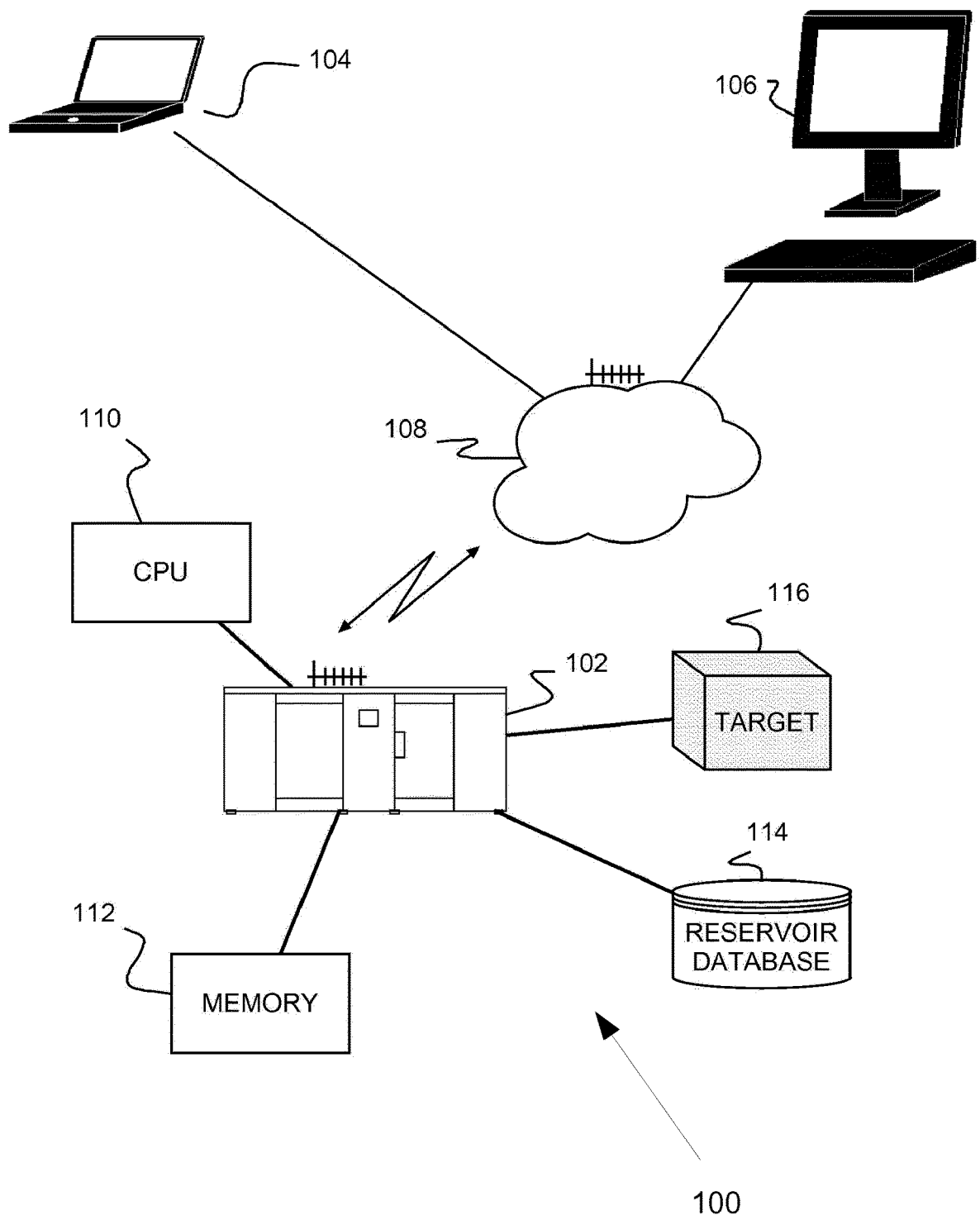
FIG. 1 This figure shows an example of a preferred appraisal system for automatically selecting a target fluid with existing analogous members stored in a analog data base according to a preferred embodiment of the present invention.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Turning now to the drawings and more particularly, FIG. 1 shows an example of an appraisal system (100) determining the fluid properties of a target fluid (e.g., in a newly discovered hydrocarbon reservoir), based on automatic pairing with cataloged and characterized existing population analogue fluid members according to a preferred embodiment of the present invention. The appraisal system (100) includes computers (102, 104, 106) (3 in this example) coupled, wired or wirelessly to, and communicate with each other over, network 108, e.g., a local area network (LAN), the Internet, an intranet or a combination thereof. Typically, the computers (102, 104, 106) include one or more processors, e.g., central processing unit (CPU) (110), memory (112) and local storage (114) with a catalog listing known or existing analogue fluid members and fluid or reservoir properties e.g., a reservoirs database.

In this example, the fluid property generation will be based on the proposed correlations and the knowledge provided by the analogue data base stored in the local storage (114) that will be used for correcting the proposed correlations $c_i$ in order to meet as much as possible with the fluid properties stored within the stored analogue data base.

Target fluid (116) properties and properties of analogue data base (114) may comprise binary properties, multiple binary properties or quantitative properties.

FIG. 2 displays a table showing a single record, shortened with a few properties for this example, with two columns, a first column with the parameters of a fluid, the target fluid (116) or an analogue fluid (114), and a second column with the value of the parameter.

Among the parameters of the record represented in FIG. 2 are the Fluid ID, the reservoir ID, using integer values for identifying the fluid and the reservoir respectively, the API Gravity value being a quantitative value, the GOR value being a quantitative value, the Kerogen Type being a multiple binary value, the Source Rock being a multiple binary value, the Source Rock Period being a multiple binary variable, the Maturation Level being a quantitative value and, a binary variable indicating if there is a fluid mixing Evidence and a binary variable indicating if washing evidence exists. These last two binary variables can be represented by a Boolean value and also by using an integer value, typically 1 and 0 according to a pre-established convention.

Maturation Level shows a question mark as the shown record does not contain the Maturation Level value. Records of the analogous data base may contain one or more parameters identifying a specific property with no value. Because of this, the rules for comparing a target fluid (116) and an analogous fluid first require to identify if a determined common parameter exists in both fluids.

Even if along the entire description the set of fluid properties are identified as such, fluid properties, said properties must be interpreted in a general form wherein some of these variables are not necessarily physical properties of a fluid but properties of the reservoir where the fluid is located or the rock storing the fluid as all of these parameters allow the characterization of the fluid.

According to this definition, the fluid characterization by generating the fluid properties takes into account the geochemistry.

Figure 3:
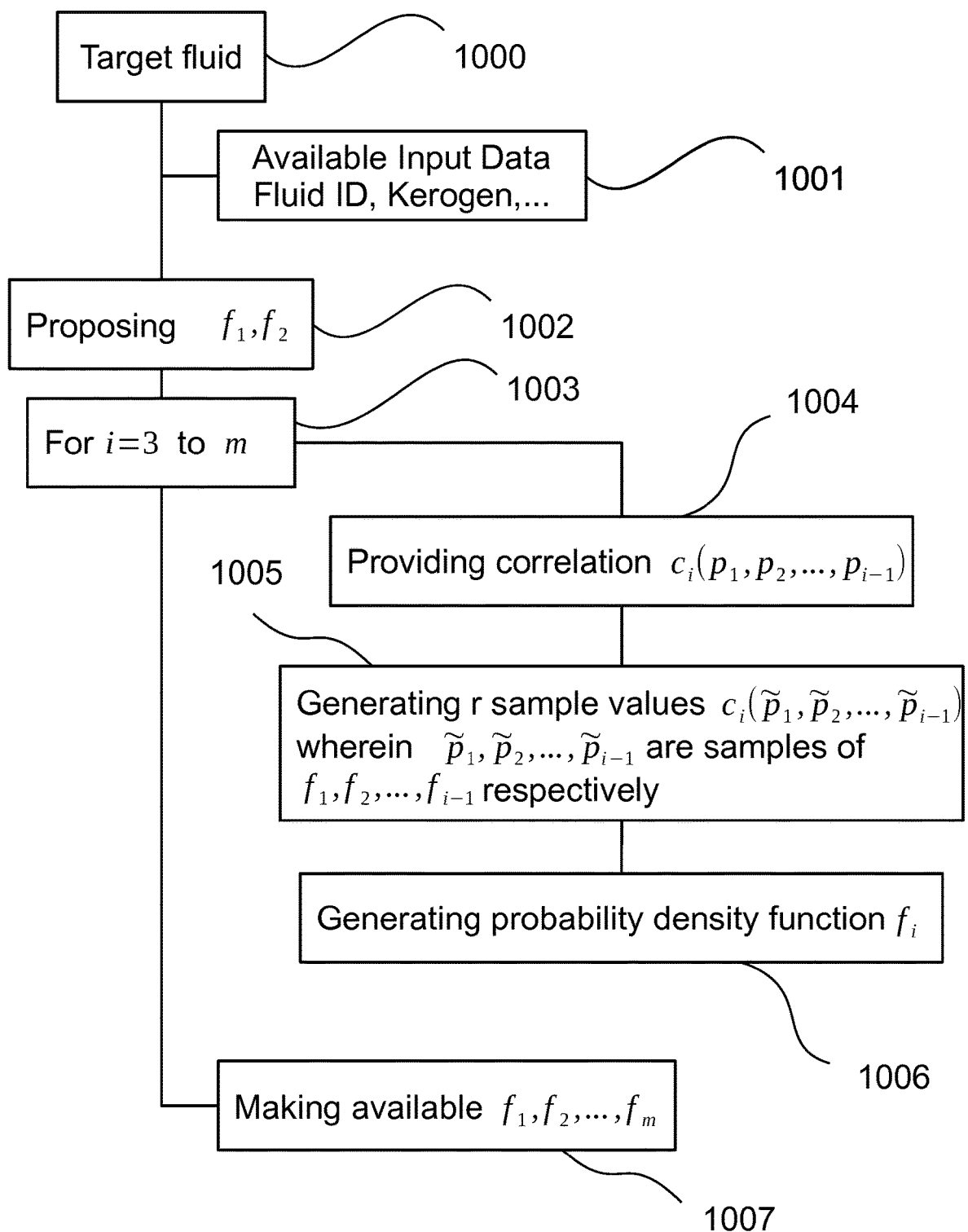
FIG. 3 This figure shows a flowchart with the main steps of an embodiment of the present invention.

In this example and turning now to FIG. 3, the preferred system (100) first determines a first fluid property ($p_1$), the API gravity of the liquid phase of the target fluid (116), and a second fluid property ($p_2$) directed to the gas/liquid ratio of the target fluid (116), the GOR property. In an embodiment, the API gravity of the liquid phase of the target fluid (116) and GOR property is obtained from the information provided by the Basin Modeling or any other predicting model.

As it is shown in the first step (1000), system (100) also comprises the following steps:

a) As it is shown in FIG. 3, in the first step (1000) the target fluid (1000) is identified with the available input data (1001), the Fluid ID, the reservoir ID, and other parameters with properties that may be obtained for instance by laboratory assays or from samples obtained when drilling a wellbore in the reservoir.

b) In a second step (1002) and in this embodiment the system (100) determines a probability density function ($f_1$) for the API gravity ($p_1$) and a probability density function ($f_2$) for the GOR property ($p_2$) characterizing these two first properties of the target fluid.

In this particular case, a uniform probability density function is used for $f_1$ and $f_2$.

c) In a third step (1003), m−2 correlations $c_3, \ldots, c_m$ are provided, said correlations dependent at least on $p_1$ and/or $p_2$ properties, wherein additional dependencies may exist, that is, $p_i = c_i(p_1, p_2 \ldots, p_{i-1})$; i=3, ..., m. FIG. 3 shows an iterator i value ranging from 3 to m wherein for each iterator value three sub-steps (1004, 1005) are executed:

a first sub-step (1004) wherein the identified $c_i(\tilde{p}_1, \tilde{p}_2, \ldots, \tilde{p}_{i-1})$ correlations are provided, a second sub-step (1005) generating, automatically by the computer system (100), r sample values $c_i(\tilde{p}_1, \tilde{p}_2, \ldots, \tilde{p}_{i-1})$ wherein $\tilde{p}_1, \tilde{p}_2, \ldots, \tilde{p}_{i-1}$ are random samples according to their corresponding probability density functions $f_1, f_2, \ldots, f_{i-1}$. That is, each property $p_j$, among those properties $\tilde{p}_1, \tilde{p}_2, \ldots, \tilde{p}_{i-i}$ appearing explicitly in the dependency of $c_i$, is sampled using the corresponding probability density function $f_j$. Those samples are introduced in the correlation $c_i$ for calculating each sample of $c_i(\tilde{p}_1, \tilde{p}_2, \ldots, \tilde{p}_{i-1})$ and, a third sub-step (1006) generating, automatically by the computer system (100), a probability density function $f_i$ for property $p_i$ from the r sample values $c_i(\tilde{p}_1, \tilde{p}_2)$. In this particular case, the r sample values allow to compute frequencies of sub-ranges according to a discretization of the domain for the property values providing a numerical approximation of the probability density function.

d) In a forth step (1007) the method makes available the characterizing properties $p_i$, i=1, ..., m of the fluid as the probability density functions ($f_1, f_2, \ldots, f_m$) being determined in step b) (1002) and the third sub-step (1006).

In this example correlations $c_i(\tilde{p}_1, \tilde{p}_2, \ldots, \tilde{p}_{i-1})$ are dependent on $\tilde{p}_1$ and/or $\tilde{p}_2$ and other dependencies $\tilde{p}_j$, j=3, ..., i−1 may exist.

According to this preferred embodiment, correlations $c_i$ provided in the first sub-step (1004) are modified by a shift value and a scaling value in order to force the correlation being a good representation of the analog fluids.

In a first step, given the target fluid (116), a set of analogue fluids are identified and selected by implementing a similarity module which selects those records of the stored analogue data base (114) complying a similarity criteria, that is, given a threshold value (sim).

Once a sub-set of records of the analogue data base are selected, the modified correlation $c'_i$ being expressed as $c'_i = c_i * C + \Delta c_i$, being C and $\Delta c_i$ constant values, said constant values are determined by imposing that the sum of the errors between the value provided by the new correlation $c'_i$ and the property value provided by each of the selected records of the analog data base is minimum.

In this adjustment process the selecting criterion is very relevant as it allows determining only those records that provide valuable information of the target fluid (116). A certain correlation $c_i$ involves properties $p_j$ j=1 ... i but selected records of the analogues data base, when computing the modified correlation $c'_i$, comprises additional properties such as geological, chemical and physical properties. These additional properties provide a contribution on the adjusting process improving the final expression $c'_i = c_i * C + \Delta c_i$ because of the influence of these additional parameters when selecting the analogous records.

In this selection process, geological, chemical and physical properties of the fluid and the reservoir are assessed by identifying binary properties, multiple binary properties and quantitative properties. Each of these three kind of properties provide a contribution value and, all contribution values are weighed for computing the similarity value being used for assessing the distance between the target fluid and each of the records of the fluid of the analogue data base.

Once all distances identified as a similarity index has been computed the analogue fluids are ranked by said similarity index. The selected analogue fluids are those satisfying that the absolute value of the similarity index is higher than the threshold value (sim).

In this particular example the similarity value $s_{ij}$ between a target fluid and a record from the analog data base, taking into account the contribution of the three kinds of properties is computed as $$s_{ij} = \frac{\sum_{h=1}^{Vc}\left(\left(1 - \frac{|Vc_{ih} - Vc_{jh}|}{G_h}\right)Pc_h\right) + \sum_{k=1}^{Vb}(Vb_k * Pb_k) + \sum_{l=1}^{Vmb}(Vmb_l * Pmb_l)}{Pc_t + Pb_t + Pmb_t}$$

wherein

Vc is the number of quantitative variables of the target fluid;

$Vc_{ih}$ is the $h^{th}$ fluid quantitative property $Vc_i$ of the target fluid among the Vc quantitative properties of the target fluid;

$Vc_{jh}$ is the $h^{th}$ fluid quantitative property $Vc_j$ of the analog record among the Vc quantitative properties of the target fluid;

$Pc_h$ is a weighing value of the $h^{th}$ quantitative variable;

$G_h$ is the common range of the $h^{th}$ quantitative variables $Vc_i$ and $Vc_j$;

Vb is the number of binary variables of the target fluid;

$Vb_k$ is a coincidence value, 1 if there is coincidence or 0 otherwise, for the $k^{th}$ binary variable of the target fluid;

$Pb_k$ is a weighing value for the $k^{th}$ binary variable

Vmb is the number of multiple binary variables of the target fluid;

$Vmb_l$ is a coincidence value, 1 if there is coincidence or 0 otherwise, for the $l^{th}$ multiple binary variable of the target fluid;

Pmb$_l$ is a weighing value of the $l^{th}$ multiple binary variable;
Pc$_t$ is the total weight of the quantitative variables;
Pb$_t$ is the total weight of the binary variables;
Pmb$_t$ is the total weight of the multiple binary variables.

FIG. 4 shows a table with three binary variables, a property indicating if there is TSR evidence, a property indicating if there is washing evidence and a property indicating if there is fluid mixing evidence.

Each type of binary variable has assigned an integer value, 0 or 1, identifying each Boolean value allowing computing the property when compared to other properties such as the quantitative properties.

These three binary properties are compared with records having a parameter identifying said properties.

The numerator of the expression used for the computation of the similarity value $s_{ij}$ shows the term $\Sigma_{k=1}^{Vb}(Vb_k*Pb_k)$ as the binary contribution value. This contribution value is being weighed by Pb$_k$, the weighing value for the $k^{th}$ binary variable.

FIG. 5 shows a table with two multiple binary variables, a property indicating the Kerogen Type of the fluid and property indicating the Source Rock.

Each type of multiple binary variables has assigned an integer value, 0 or 1, identifying each type allowing computing the property when compared to other properties such as the quantitative properties.

The same numerator of the expression used for the computation of the similarity value $s_{ij}$ shows the term $\Sigma_{l=1}^{Vmb}(Vmb_l*Pmb_l)$ as the multiple binary contribution value. This contribution value is being weighed by Pmb$_l$, the weighing value of the $l^{th}$ multiple binary variable.

And finally, the same numerator of the expression used for the computation of the similarity value $s_{ij}$ shows the term $$\sum_{h=1}^{Vc}\left(\left(1-\frac{|Vc_{ih}-Vc_{jh}|}{G_h}\right)Pc_h\right)$$

as the quantitative contribution value. This contribution value is being weighed by Pc$_h$, the weighing value of the $h^{th}$ quantitative variable.

FIGS. 6A-6D show four tables with four quantitative properties respectively, only as an example, the Fluid ID, the Source Rock Period and the Maturation Level. The right column shows the value of each parameter.

The computed similarity value $s_{ij}$ is being divided by three total weights,

Pc$_t$+Pb$_t$+Pmb$_t$ normalizing the similarity value $s_{ij}$.

In each type of variables the weighing value is being penalized if there is no datum in the analogue record or for the target fluid.

Each property has an associated value (being 0 or 1 for binary properties and multiple binary properties) that then is multiplied by a weighing value.

For quantitative values, the value of each quantitative variable is determined by the following factor:

$$\left(1-\frac{|Vc_{ih}-Vc_{jh}|}{G_h}\right)$$

and being weighed by the weighing value Pc$_h$ resulting the term $$\sum_{h=1}^{Vc}\left(\left(1-\frac{|Vc_{ih}-Vc_{jh}|}{G_h}\right)Pc_h\right)$$

already indicated above.

Factor $(1-|Vc_{ih}-Vc_{jh}|/G_h)$ is the difference of the analogue value and the target value when compared to the total range of the variable. This difference ranging [0,1] multiply the weighing value of each variable providing part of the value or the whole value.

For instance, the variable biodegradation is quantitative and has a weight of 13%. The range $G_h$ is 9 because it ranges from 1 to 10. If the target fluid has a biodegradation value of 1 and the analogue fluid has a value of 3, the difference is the absolute value of $Vc_{ih}-Vc_{jh}$ that will result as 2. This result divided by $G_h$ (9) results is 0.222. The difference 1−0.222 is 0.788, the factor multiplying the weight of the biodegradation variable (13%). Therefore, the final result of the contribution of the quantitative biodegradation variable for this specific analogue record is 10.11%.

The denominator of the similarity value $s_{ij}$ has the weight of all variables being the maximum value 100%.

Figure 7:
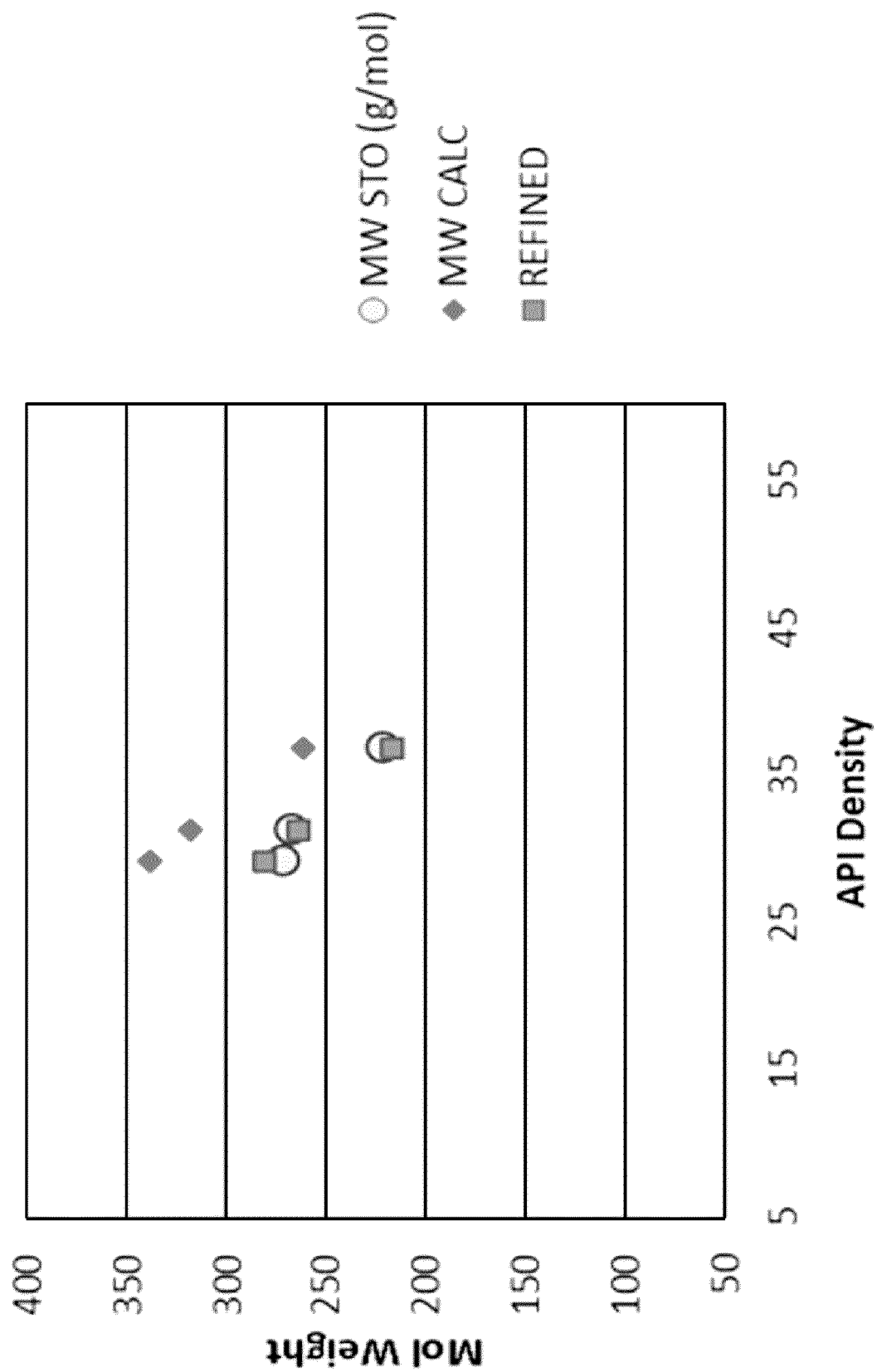
FIG. 7 This figure shows a graphic displaying the Molecular Weight obtained in three identified analogue records, the Molecular Weight obtained by using the correlation and the Molecular Weight obtained by the correlation once it has been modified by shifting and scaling.

FIG. 7 shows an embodiment wherein three different analogous records have been identified with the target fluid. These three records comprise the API gravity property (API) and the Molecular Weight property (MW), the $i^{th}$ property being generated according to an embodiment of the invention. The proposed correlation $c_i$ for the Molecular Weight property is MW=630−(10*API).

The modified correlation may be expressed in the form

MW=C[630−(10*API)]+Δc$_i$ being C and Δc$_i$ constants to be determined by minimizing the sum of relative errors between the result of the modified correlation and the values of the properties of the analogue fluid.

In this embodiment, C results 0.83 and Δc$_i$ results 0 (no need of shifting); that is, the modified correlation is MW=0.83*[630−(10*API)]

FIG. 7 shows three different results, the Molecular Weight calculated (small diamonds) by using the original correlation, the Molecular Weight of the selected analogue fluids (circles) and the Molecular Weight calculated (squares) by using the modified correlation.

The modified correlation is strongly dependent on the selection of analogue records, being this selection being carried out by using the disclosed method depending on the type of properties and the definition of the similarity value $s_{ij}$.

The modified correlation for MW is then used in step c) of the invention when generating, automatically by a computer system, a probability density function $f_i$ for property $p_i$ from the r sample values calculated from MW (API).

A practical application of the characterizing method of a target fluid is the generation of fluid properties in a hydrocarbon reservoir for assessing the viability of fluid production from said reservoir throughout predetermined field architecture under uncertainty of the fluid properties.

When the facilities to be deployed in a field are designed, parameters as the dimensions of the pipes to be used, the path of said pipes from the reservoir to the surface, the thickness of the thermal insulation must be defined. Such parameters are determined according to the fluid properties as when the fluid flows from the reservoir to the surface, temperature and pressure decreases bringing on the appearance of solid phases that may prevent the normal flow of the fluid.

In an embodiment of the invention, a method for assessing the viability of fluid production in a hydrocarbon reservoir and for certain facilities comprising at least one pipe connecting a first point of extraction located within the reservoir and a final end point located at surface facilities is proposed. The method comprises the following steps:

determining a temperature and pressure (T,P) domain for representing the behavior of the fluid along the piping of the facilities.

The path of the piping to be assessed is already determined. Real measurements and numerical production models are examples of means providing the temperature and pressure along a predetermined domain, in particular along the piping production system.

establishing regions as risk regions in the (T,P) domain where the temperature and pressure variables (T,P) are such as the fluid shows a phase transition.

Examples of regions having a risk in the (T,P) domain are those regions where the fluid shows a change of phase for instance solid appearance. Additional risk regions may be established, for instance regions where the viscosity is too high to ensure the flow.

determining a fluid defined by a set of properties $p_1$, $p_2 \ldots, p_m$ under uncertainty according to any of the embodiments already disclosed, wherein each property $j \in [1, m]$ can take values in a range $[a_j, b_j]$ and it is defined from at least a discrete value of its probability density function, and wherein at least one of property is the first fluid property $p_1$;

generating two samples of fluid, a first sample of low density $f^l$ and a second sample of high density $f^h$;

In this step the fluid is being characterized by defining probability density functions of each fluid property departing from two ($p_1$, $p_2$) properties, in particular these properties may be the API gravity and GOR which allows to define a low density $f^l$ and a high density flow $f^h$.

providing a module for the simulation in a computer system of the evolution of a fluid along the piping of the facilities for a predetermined flow rate, said piping comprising one or more pipes defined at least by the diameter, length, degree of thermal insulation and ambient temperature;

simulating, by means of the module for the simulation, the evolution of the first sample of fluid $f^l$ and the evolution of the second sample of fluid $f^h$ along the piping of the facilities providing a first path and a second path respectively of the evolution in the (T,P) domain;

The evolution of the low density $f^l$ along the piping of the facilities and the evolution of the high density flow $f^l$ along the same piping of the facilities provides two separated trajectories of the flow in the temperature and pressure (T,P) domain and a region between both trajectories. The evolution of the two fluids ($f^l$, $f^h$) is computed by the module for the simulation as the piping and other parameters of the facilities are already determined, the facilities being assessed.

if the first path and the second path do not fall within any of the risk regions then the field architecture is determined as viable for any fluid with densities between the low density and the high density chosen on step c), otherwise the field architecture is determined as not being viable.

The proposed method avoids the assessing of the entire region defined between the two trajectories of the two fluids ($f^l$, $f^h$) and only the first trajectory or path in the (T,P) domain taking into account the evolution of the first sample of fluid $f^l$ and the second trajectory or path in the (T,P) domain taking into account the evolution of the second sample of fluid $f^h$ are checked, verifying if any of these trajectories or paths fall within any of the already determined risk regions. If this is the case, the field architecture is determined as not being viable.

When a field architecture defined by the facilities designed to be deployed in the field is determined as not being viable then said facilities must be re-designed for instance at the locations corresponding to the (T,P) domain falling within a risk region or, changing the entire flow conditions like the pump system.

Once the field architecture is redefined the proposed method may be used again for assessing the viability of fluid production with the new facilities.

The invention claimed is:

1. A computer implemented method for assessing the viability of fluid production from a hydrocarbon reservoir using characteristics of a target fluid present within the hydrocarbon reservoir, wherein characterization of the target fluid, at least in part, is determined based on properties of the hydrocarbon reservoir in which the target fluid is located, or on properties of the hydrocarbon reservoir rock that stores the target fluid, and the viability of fluid production is simulated through facilities of the reservoir having a predetermined field architecture including at least one pipe connecting a first point of fluid extraction located within the reservoir and a final end point of fluid extraction located at surface facilities of the reservoir, the method comprising the following steps:

a) establishing m predetermined fluid properties ($p_1$, $p_2, \ldots, p_m$) including at least a first fluid property ($p_1$) directed to one of the phases of the target fluid present in the hydrocarbon reservoir, either liquid or gas, and a second fluid property ($p_2$) directed to a gas/liquid ratio of the target fluid;

b) assigning a probability density function ($f_1$) for the first fluid property ($p_1$) and a probability density function ($f_2$) for the second fluid property ($p_2$);

c) providing m−2 correlations $c_3, \ldots, c_m$ dependent at least on $p_1$ and/or $p_2$ properties such that $p_i = c_i(p_1, p_2)$; $i = 3, \ldots, m$;

d) for each property $p_i$, $i = 3, \ldots, m$
generating, automatically by a computer system, r sample values $c_i(\tilde{p}_1, \tilde{p}_2)$ wherein $\tilde{p}_1$ is a random sample according to its probability density function $f_1$ and $\tilde{p}_2$ is a random sample according to its probability density function $f_2$;
generating, automatically by a computer system, a probability density function $f_i$ for property $p_i$ from the r sample values $c_i(\tilde{p}_1, \tilde{p}_2)$;

e) based on the probability density functions ($f_1$, $f_2, \ldots, f_m$), determining the characterizing properties $p_i$, $i = 1, \ldots, m$ of the target fluid present in the hydrocarbon reservoir;

f) using the characterizing properties of the target fluid determined in step e), assessing the fluid production viability of the reservoir by simulating the evolution of the target fluid along the piping of the predetermined field architecture.

2. The method according to claim 1 wherein the first fluid property ($p_1$) directed to one of the phases of the target fluid is the American Petroleum Institute (API) gravity and the second fluid property ($p_2$) directed to the gas/liquid ratio of the target fluid is the gas-oil ratio (GOR) ratio.

3. The method according to claim 1, wherein correlation $c_i(p_1, p_2)$ also depends on at least one additional fluid property $p_j$, being $j<i$.

4. The method according to claim 3, wherein the fluid properties $p_i$, i=3, . . . , m are sorted such that dependency of correlations is $c_3=c_3(p_1, p_2)$, $c_4=c_4(p_1, p_2, p_3)$, . . . , $c_i=c_i(p_1, p_2, \ldots, p_{i-1})$ wherein not necessarily all properties $p_3, \ldots, p_{i-1}$ appear as dependent parameters.

5. The method according to claim 1, wherein it further comprises
providing an analog data base, said analog data base executable in a computer system, comprising records of fluids with fluid properties from known reservoirs, wherein at least one record of the analog data base further comprises the first fluid property ($p_1$), the second fluid property ($p_2$) or both;
providing a similarity module for the comparison of fluid properties of the target fluid and fluid properties of records of the analog data base, the module providing a similarity value as a result of said comparison,
wherein before determining a property $p_i$ by generating r sample values in step c), i being an integer value in the interval [3,m], the following steps are carried out:
i. determining a threshold parameter (sim);
ii. selecting the set of records of the analog data base, by means of the similarity module, having a similarity value higher than the threshold parameter (sim) when compared to a target fluid,
iii. determining a modified correlation $c'_i$ as $c'_i=c_i*C+\Delta c_i$, being C and $\Delta c_i$ constant values, said constant values being determined by imposing that the sum of the errors between the value provided by the new correlation $c'_i$ and the property value provided by each of the selected records of the analog data base is minimum;
iv. in step c) using the modified correlation $c'_i$ when the r sample values $c_i(\tilde{p}_1, \tilde{p}_2)$ are computed.

6. The method according to claim 5, wherein the properties compared between the target fluid and the records of the analog data base comprises geochemical properties, thermodynamic properties or both, said properties being quantitative, multiple binary or binary variables or any combination thereof.

7. The method according to claim 5, wherein the target fluid and at least one record of the analogous data base comprise at least one binary property wherein
each type of the binary properties is set to 0 or 1 and comprises a weighing value and
the similarity module comprises a binary property contribution value, said contribution value being weighed with the weighing value, said weighing value determined according to the following rules for each binary property:
if the target fluid does not have the binary property and/or the record does not have the binary property, then the contribution value to the similarity value is set to 0 and the weighing value of the binary property is not taken into account;
if the target fluid and the record have the binary property but the target fluid value is different to the record value the contribution value to the similarity value is set to 0 so it does not account the weighing value of the property;
if the target fluid and the record have the binary property and the target fluid value is equal to the record value the weighing value is set to 1 so the full weighing value of the property is the contribution value to the similarity value.

8. The method according to claim 5, wherein the target fluid and at least one record of the analogous data base comprise at least one multiple binary property wherein
each type of the multiple binary properties is set to 0 or 1 and comprises a weighing value and
the similarity module comprises a multiple binary property contribution value, said contribution value being weighed with the weighing value, said weighing value determined according to the following rules for each multiple binary property:
if the target fluid does not have the multiple binary property and/or the record does not have the multiple binary property, then the contribution value to the similarity value is set to 0 and the weighing value of the multiple binary property is not taken into account;
if the target fluid and the record have not in common any of the multiple integer combination of values, the contribution value to the similarity value is set to 0 and the weighing value of the property is not taken into account;
if the target fluid and the record have in common at least one of the multiple integer combination of values, the weighing value is set to 1 so the full weighing value of the property is the contribution value to the similarity value.

9. The method according to claim 5, wherein the target fluid and at least one record of the analogous data base comprise at least one quantitative property wherein
each type of the quantitative properties has a continuous value and comprises a weighing value and,
the similarity module comprises a quantitative property contribution value, said contribution value being weighed with the weighing value, said weighing value determined according to the following rules for each quantitative property:
if the target fluid does not have the continuous value property and/or the record does not have the continuous value property, then the contribution value to the similarity value is set to 0 and the weighing value of the quantitative property is not taken into account;
if the target fluid and the record have the same quantitative property the contribution value to the similarity value is weighed by the weighing value:

$$\left(1 - \frac{|Vc_{ih} - Vc_{jh}|}{G_h}\right)$$

wherein
$Vc_{ih}$ is the $h^{th}$ fluid quantitative property $Vc_i$ of the target fluid among the Vc quantitative properties of the target fluid, being Vc the number of quantitative variables of the target fluid;
$Vc_{jh}$ is the $h^{th}$ fluid quantitative property $Vc_j$ of the analog record among the Vc quantitative properties of the target fluid; and
$G_h$ is the common range of the $h^{th}$ quantitative variables $Vc_i$ and $Vc_j$.

10. The method according to claim 5, wherein the similarity value $s_{ij}$ between a target fluid and a record from the analog data base is computed as $$s_{ij} = \frac{\sum_{h=1}^{Vc}\left(\left(1 - \frac{|Vc_{ih} - Vc_{jh}|}{G_h}\right)Pc_h\right) + \sum_{k=1}^{Vb}(Vb_k * Pb_k) + \sum_{l=1}^{Vmb}(Vmb_l * Pmb_l)}{Pc_t + Pb_t + Pmb_t}$$

wherein

Vc is the number of quantitative variables of the target fluid;

$Vc_{ih}$ is the $h^{th}$ fluid quantitative property $Vc_i$ of the target fluid among the Vc quantitative properties of the target fluid;

$Vc_{jh}$ is the $h^{th}$ fluid quantitative property $Vc_j$ of the analog record among the Vc quantitative properties of the target fluid;

$Pc_h$ is a weighing value of the $h^{th}$ quantitative variable;

$G_h$ is the common range of the $h^{th}$ quantitative variables $Vc_i$ and $Vc_j$;

Vb is the number of binary variables of the target fluid;

$Vb_k$ is a coincidence value, 1 if there is coincidence or 0 otherwise, for the $k^{th}$ binary variable of the target fluid;

$Pb_k$ is a weighing value for the $k^{th}$ binary variable

Vmb is the number of multiple binary variables of the target fluid;

$Vmb_l$ is a coincidence value, 1 if there is coincidence or 0 otherwise, for the $l^{th}$ multiple binary variable of the target fluid;

$Pmb_l$ is a weighing value of the $l^{th}$ multiple binary variable;

$Pc_t$ is the total weight of the quantitative variables;

$Pb_t$ is the total weight of the binary variables;

$Pmb_t$ is the total weight of the multiple binary variables.

11. The method according to claim 1, wherein the probability density function characterizing a determined property is expressed as:
- a piecewise probability density function,
- two or more percentile measures or,
- both.

12. The method according to claim 1 wherein $f_1$ and $f_2$ are uniform distributions.

13. The method according to claim 1 wherein at least one correlation $c_i$ comprises thermodynamic properties.

14. The method according to claim 1, wherein the $p_j$ property is defined by three percentiles, a $p_{low}$-percentile, a $p_{mean}$-percentile and a $p_{high}$-percentile.

15. The method according to claim 1, further comprising:
- determining a temperature and pressure (T,P) domain for representing the behavior of the fluid along the piping of the facilities;
- establishing regions as risk regions in the (T,P) domain where the temperature and pressure variables (T,P) are such as the fluid shows a phase transition;
- determining a fluid defined by a set of properties $p_1$, $p_2, \ldots, p_m$ according to claim 1, wherein each property $j \in [1, m]$ can take values in a range $[a_j, b_j]$ and it is defined from at least a discrete value of its probability density function, and wherein at least one of properties is the first fluid property $p_1$;
- generating two samples of fluid, a first sample of low density $f^l$ and a second sample of high density $f^h$;
- providing a module for the simulation in a computer system of the evolution of a fluid along the piping of the facilities for a predetermined flow rate, said piping comprising one or more pipes defined at least by the diameter, length, degree of thermal insulation and ambient temperature;
- simulating, by means of the module for the simulation, the evolution of the first sample of fluid $f^l$ and the evolution of the second sample of fluid $f^h$ along the piping of the facilities providing a first path and a second path respectively of the evolution in the (T,P) domain;
- if the first path and the second path do not fall within any of the risk regions then the field architecture is determined as viable for any fluid with densities between the low density and the high density chosen on step c), otherwise the field architecture is determined as not being viable.

16. A computer program product stored on a non-transitory computer-readable medium and comprising computer-implementable instructions which, when executed by a computer, cause the computer to carry out the method according to claim 1.

* * * * *